US00PP07994P

United States Patent [19]

Moore

[11] Patent Number: Plant 7,994

[45] Date of Patent: Oct. 6, 1992

[54] MINIATURE ROSE PLANT NAMED 'MORHILL'

[75] Inventor: Ralph S. Moore, Visalia, Calif.

[73] Assignee: Sequoia Nursery, Visalia, Calif.

[21] Appl. No.: 648,980

[22] Filed: Jan. 31, 1991

[51] Int. Cl.[5] ..... A01H 5/00

[52] U.S. Cl. ..... Plt./7.1

[58] Field of Search ..... Plt. 7-9

[56] References Cited

U.S. PATENT DOCUMENTS

P.P. 3,860 4/1976 Williams ..... Plt. 7

P.P. 4,636 2/1981 Strawn ..... Plt. 7

*Primary Examiner*—Howard J. Locker

[57] ABSTRACT

This invention relates to a new and distinct variety of miniature rose plant primarily identified by its very double flowers with the petals being a blend of pink and yellow.

1 Drawing Sheet

The present invention relates to a new and distinct variety of hardy, dwarf, bush type rose plant of the miniature class; the variety being primarily characterized — as to novelty — by the very double flowers, the petals being a blend of pink and yellow.

The variety is further characterized by:

An abundance of blooms, with flowers usually borne several to the stem in loose clusters or sprays, but also sometimes singly. Sepals: permanent; spear shaped; recurved.

Some fragrance.

A plant which is vigorous, of rounded to bushy shape with small semi-glossy foliage with pointed leaflets; the buds and flowers being similar in form to Pink Petticoat (miniature — U.S. Plant Pat. No. 4,636).

The plant, which has a normal height of 12-14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery, located at Visalia, Calif., under conditions of careful control and observation, as a cross between Little Darling (U.S. Plant Pat. No. 1,581), as the seed parent and Golden Angel (miniature — U.S. Plant Pat. No. 4,028) as the pollen parent.

Subsequent to origination of the variety I successfully asexually reproduced it at the same nursery, located as aforesaid, by budding as well as by cuttings; the reproductions having run true in all respects.

The color photograph illustrates the variety including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded to upright; seedling; greenhouse; outdoors; cut flowers; garden decoration; potted plant.

Class: Miniature.

*Variety identification.*—MORhill.

*Commercial synonym.*—MARY HILL.

Flowers borne: Several together in loose clusters or spray, sometimes singly, on sturdy, wirey stems.

Quantity of bloom: Abundant both outside and in greenhouse.

Bud:

*Peduncle.*—Medium length; slender but sturdy; erect; medium green, sometimes tinted bronze (outdoors); with numerous small hair-like appendages.

*Before calyx breaks.*—Size — Small. Form — Ovoid to pointed, with several small foliaceous parts extending beyond the tip of the bud equal to one-half or less of its length. Color — Medium green, occasionally tinted with bronze (outdoors).

*As calyx breaks.*—Color — Pink.

*Opening.*—Opens well in all weather.

Bloom:

*Size when fully open.*—Small, averaging about 45 mm (1¾").

*Petalage.*—Very double — Averaging about 65 (or more) petals, arranged regularly plus several small petaloids.

*Form.*—Full, high centered — First becoming rounded with petals rolled loosely outward and downward. Open flowers usually have few or no stamens.

Petals: Fairly thick; satiny on inside and on outside surface.

*Shape.*—Outside petals — Broad lanceolate (wedge shaped) with rounded tip; Intermediate — Broad lanceolate with nearly round or short acute tip; Inside — Lanceolate with short acute tip.

Color: Newly opened flower from a plant grown outdoors (October, 1990), Visalia, Calif.:

*Outside petal.*—Outside surface — Red/pink (near Carmine 21/1 or lighter) blending into yellow (near Empire Yellow 603/2 at base). Inside surface — Near Crimson 22/1 or Crimson 22/2 blending into yellow (near Empire Yellow 603/1 at base).

*Intermediate petal.*—Outside surface similar to outside petal. Inside surface to outside petal.

*Inner petal.*—Outside — Similar to intermediate petal; Inside surface — Similar to intermediate petal.

*General color effect.*—Newly opened flowers — Medium pink with lighter reverse. Three days open — Color — Similar to fresh open flower, but less bright (more pink).

Behavior: Opens well in all weather. Spent petals or flowers drop off.

Flower longevity (October, 1990): Plant in pot 8–10 days or longer. Cut flowers at living room temperature 4–5 days or longer.

Reproductive organs:

*Stamens.*—Few or none.

*Filaments.*—Few or none.

*Anthers.*—Few or none.

*Pollen.*—Little or none.

*Pistils.*—Small number, bunched.

*Styles.*—Short length; yellowish; varying length; bunched.

*Ovaries.*—All enclosed in calyx.

*Hips.*—None.

*Seed.*—None.

Foliage:

*Leaves.*—Compound of five (sometimes three or seven) leaflets; medium small; leathery; semi-glossy.

*Leaflets.*—Shape — Broad lanceolate; apex acute; Base — Acute — Sometimes rounded. Color-.—Medium green; New growth — Normal (medium) green (sometimes tinted reddish).

*Rachis.*—Medium strength; upperside may have a few short hairs; grooved; underside may have several small thorns (or claws) and few to several tiny short prickles.

*Stipules.*—Medium length; medium width; short length narrow points which turn out usually at about 45 degrees or less.

Growth:

*Habit.*—Dwarf; bushy; rounded; much branched.

*Growth.*—vigorous; internodes short.

*Canes.*—Medium; slender; sturdy.

*Main stems.*—Color: Medium green.

*Thorns.*—Average, of varying size and length — usually straight (at right angle to cane).

*Hairs.*—Some hairs and short prickles.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, upright, much branched habit, substantially as illustrated and described, characterized by buds and flowers, basically pink blending into yellow at the base, the bud being pointed in the early opening stage, resembling in form Pink Petticoat (miniature — U.S. Plant Pat. No. 4,636) with the open flower being very full (double) and rounded with many (65 or more) petals; and further characterized by the plant being of compact, vigorous, rounded to upright shape, with main stems and shoots of average thorniness, said plant being easy to propagate from soft wood cuttings and having an abundance of small semi-glossy foliage, the flowers being borne singly or several together in loose clusters or sprays on medium length stems.

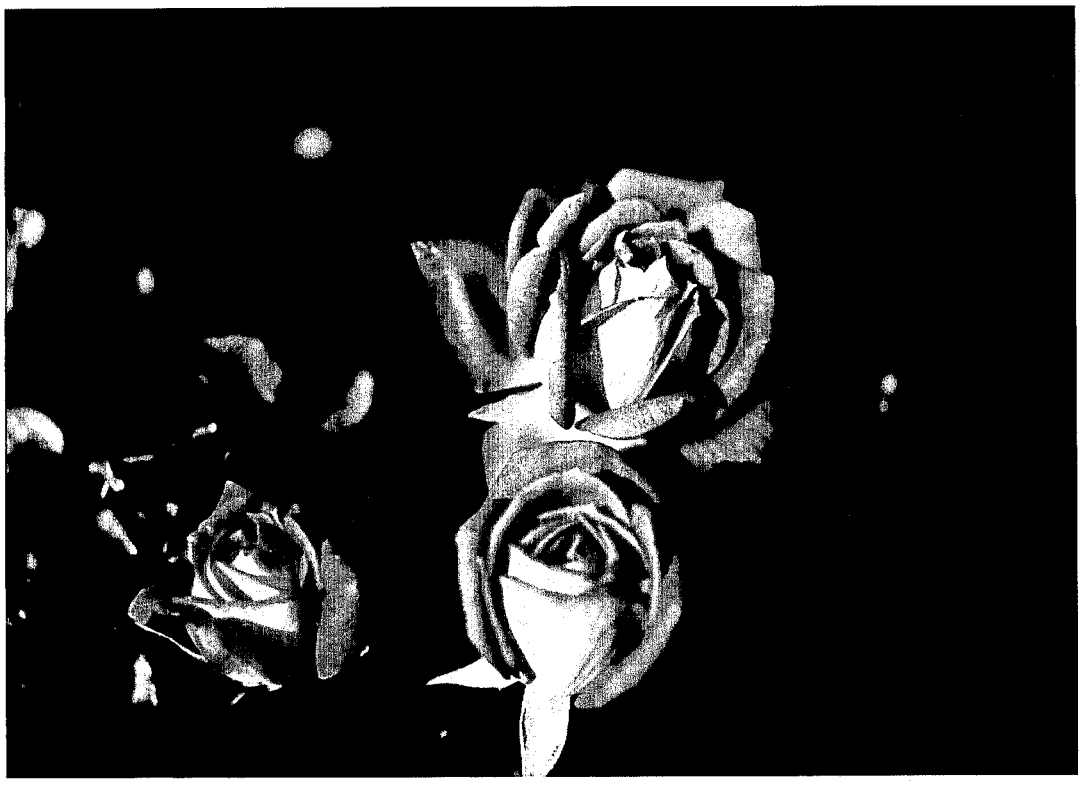

* * * * *